(12) United States Patent
Mi et al.

(10) Patent No.: US 6,586,239 B1
(45) Date of Patent: Jul. 1, 2003

(54) PURIFYING MICROGLIAL CELLS BY BINDING CELL $F_C$ RECEPTOR TO IMMUNOGLOBULIN G $F_C$ DOMAIN

(75) Inventors: Huaiyu Mi, Fremont, CA (US); Saili Yi, San Francisco, CA (US)

(73) Assignee: AGY Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 09/479,589

(22) Filed: Jan. 7, 2000

(51) Int. Cl.$^7$ .............................. C12N 5/06; C12N 5/08; C12N 1/02; C12N 11/08; C07K 17/08
(52) U.S. Cl. ...................... 435/325; 435/176; 435/180; 435/261; 435/363; 435/366; 435/395; 530/811; 530/815
(58) Field of Search ................................. 435/174, 176, 435/177, 180, 325, 395, 363, 366; 530/811, 815

(56) References Cited

U.S. PATENT DOCUMENTS 5,981,194 A * 11/1999 Jefferies et al. ............... 435/7.1

FOREIGN PATENT DOCUMENTS

EP 0 415 801 A1 3/1991

OTHER PUBLICATIONS

Walker, D.G., S.U. Kim and P.L. McGeer; Complement and Cytokine Gene Expression in Cultured Microglia Detived From Postmortem Human Brains; *Journal of Neuroscience Research* 40 pp. 478–493; 1995.
Fong, Sherman, Constantine D. Tsoukas, Jean–Louis Pasquali, Robert I. Fox, Jean E. Rose, David Raiklen, Dennis A Carson and John H. Vaughan; Fractionation of Human Lymphocyte Subpopulations on Immuoglobulin Coated Petri Dishes; *Journal of Immunological Methods*; pp. 44 171–182; 1981.
International Searching Authority; Notification of Transmittal of the International Search Report or the Declaration and International Search Report; PCT/US01/00362; date of mailing Jul. 26, 2001.
Bauer et al., 1994, "Phagocytic activity of macrophages and microglial cells during the course of acute and chronic relapsing experimental autoimmune encephalomyelitis", *J. Neurosci. Res.* 38:365–75.

Bottenstein and Sato, 1979, "Growth of a rat neuroblastoma cell line inserum–free supplemented medium", *Proc. Natl. Acad. Sci. USA* 76:514–51.
Giulian et al., 1985, "Peptides from regenerating central nervous system promote specific populations of macroglia" *Proc. Natl. Acad. Sci. USA* 82:4287–4290.
Giulian and Baker, 1986, "Characterization of ameboid microglia isolated from developing mammalian brain" *Journal of Neuroscience* 6:2163–78.
Hollenbaugh et al., 1998, "Use of Monoclonal Antibodies for Expression Cloning" *Current Protocols in Molecular Biology* 6.11.1–6.11.16.
Huettner and Baughman, 1986, "Primary Culture of Identified Neurons from the Visual Cortex of Postnatal Rats" *Journal of Neuroscience* 6:3044–60.
Milligan et al., 1991, "Brain macrophages and microglia respond differently to lesions of the developing and adult visual system" *J. Comp. Neurol.* 314:124–35.
Robinson et al., 1986, "MRC OX–52: a rat T–cell antigen" *Immunology* 57:239–47.
Vedeler et al., 1994, "Fc receptor for IgG (FcR) on rat microglia" *J. Neuroimmunol* 49:19–24.

* cited by examiner

*Primary Examiner*—David M. Naff
(74) *Attorney, Agent, or Firm*—Pamela J. Sherwood; Bozicevic, Field & Francis LLP; Rebecca Taylor

(57) ABSTRACT

A method is provided for obtaining a cell population enriched in microglial cells by contacting a composition containing microglial cells with immunoglobulin immobilized on a matrix such as a polystyrene matrix before or after contact with the cells, allowing the cells to bind to the with immunoglobulin, and removing non-adherent cells to obtain a cell population containing preferably at least 95% microglial cells. The immunoglobulin may be $F_c$ domain-containing immunoglobulin G, and $F_c$ receptors of the microglial cells bind to the $F_c$ domain of immunoglobulin G. Purified $F_c$ fragments from immunoglobulin G may be used in place of immunoglobulin G. The microglial cells may be from brain tissue, and from tissue of a normal animal or tissue of an animal having a neurological disorder.

26 Claims, 3 Drawing Sheets

(1 of 3 Drawing Sheet(s) Filed in Color)

US 6,586,239 B1

PURIFYING MICROGLIAL CELLS BY BINDING CELL $F_C$ RECEPTOR TO IMMUNOGLOBULIN G $F_C$ DOMAIN

FIELD OF THE INVENTION

The invention provides methods for obtaining cell populations enriched in microglial cells. The invention finds application in the fields of medical, cell biology, and pharmacology (e.g., drug development).

BACKGROUND

Microglial cells are small neuroglial cells of monocyte lineage residing in the central nervous system. These cells are quiescent under normal physiological conditions, but become activated in areas of neural damage or inflammation, and in various neurological disorders, including stroke, Alzheimer's disease, Parkinson's disease, and multiple sclerosis (see, e.g., Gonzalez-Scarano et al., 1999, *Ann. Rev. Neurosci.* 22:219–40; Kreutzberg, 1996, *Trends Neurosci.* 19:312–18). The study and use of isolated microglial cells and purified microglial cell populations (including, for example, characterizing the interaction of these cells with the in vitro or in vivo environment and with drugs and drug candidates) will provide information useful in treating neurological disorders. Improved methods for preparing highly purified populations of microglial cells are thus useful in understanding and treating the pathological processes of disorders of the central nervous system.

BRIEF SUMMARY OF THE INVENTION

In one aspect, the invention provides a method for obtaining a cell population enriched in microglial cells. In an embodiment, the method involves contacting a composition comprising microglial cells (e.g., a dissociated tissue, such as dissociated brain) with immunoglobulin, wherein the immunoglobulin is immobilized on a matrix prior to or after said contacting allowing the microglial cells to bind the immobilized immunoglobulin; and removing non-adherent cells. In some embodiments, the resulting microglial cells are cultured on the matrix to which the immunoglobulin is immobilized.

In some embodiments of the invention the immunoglobulin comprises immunoglobulin G (IgG). Often the microglial cells to be purified and the immunoglobulin are from the same species (e.g., a mammal such as rat or human). In some embodiments, the microglial cells are be from brain (e.g., from human, rat, or mouse brain) and may be from a normal animal or from a patient or animal with a neurological disorder.

In some embodiments, the matrix is a plastic, such as polystyrene. The matrix may be in a variety of forms, e.g., in the form of a dish, coverslip, or bead.

In another aspect, the invention provides a composition comprising a microglial cells produced according to the method. Often, at least about 95% of the cells in the composition are microglial cells.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
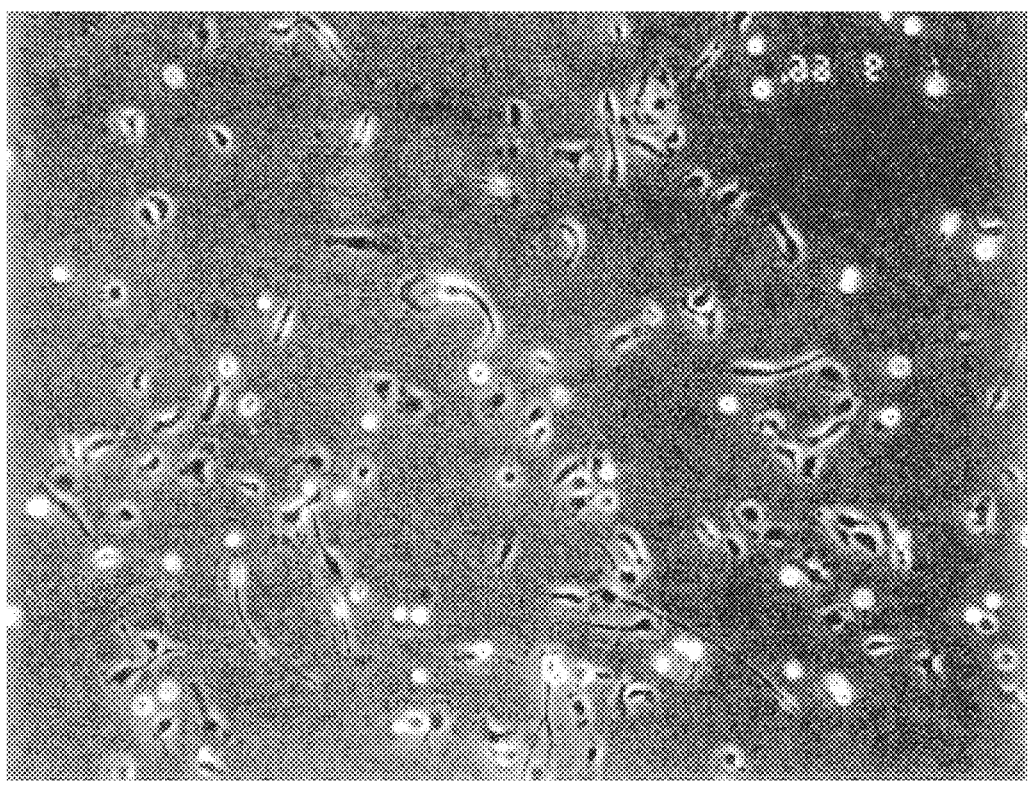
FIG. 1 shows the morphology of purified rat microglia under the phase contrast microscope. The illustration shows purified microglia on the panning dish one week after the purification and culture procedure. The cells are homogeneous, with typical microglial characteristics of large size and phase dark cell bodies with vacuoles in the cytoplasm. Scale bar: 100 μm.

The invention provides methods for rapidly obtaining highly purified microglial cells. Microglial cells are characterized by a characteristic morphology (large size and phase dark cell bodies with vacuoles under the light microscope), their ability to endocytose, and the expression of specific surface markers, such as CD11, major histocompatibility class II proteins, and scavenger receptors.

According to the method of the invention, a composition containing microglial cells (for example a suspension of disassociated brain cells) is contacted with immobilized immunoglobulin (e.g., IgG). The microglial cells adhere to the immobilized immunoglobulin, and non-adherent cells are removed. The purified microglial cells may then be dissociated from the immobilized IgG and, if desired, cultured in vitro. Alternatively, the cells may be cultured in vitro directly on the matrix to which the IgG is immobilized (e.g., without dissociation from the immobilized IgG.

The methods disclosed herein have significant advantages compared to methods currently used for microglial cell purification (summarized in, e.g., Giulian and Baker, 1986, *J. Neuroscience* 6:2163–78). The present method can be carried out in rapidly (e.g., within 4 to 6 hours, compared to 1 to 2 weeks required using other procedures), thus retaining native properties. Moreover, the present method is highly efficient, and results in a high recovery of cells. This efficiency is particularly critical when purifying cells from rare material, such as human brain tissue. In addition, the survival and growth of the cells can be monitored closely during or after the purification.

A. Tissue Sources of Microglial Cells

Microglial cells may be obtained from central nervous system (CNS) tissue (e.g., brain tissue) of mammals, including human, non-human primates, rats, mice, and other mammals. Brain tissue, or tissue from a portion or region of the brain (e.g., cortex, hippocampus) is obtained by dissection or biopsy, and the tissue dissociated into a suspension of cells by routine methods, e.g., as described infra. Suitable tissue includes tissues from normal patients or animals, patients with a neurological disorder (e.g., stroke, Alzheimer's disease, Parkinson's disease, or multiple sclerosis), or tissues from animal models of neurological disease.

B. Preparation of Cell Suspension

Tissue containing microglia (e.g., brain tissue) may be dissociated using any of a variety of methods known to preserve cell vitality. In one embodiment, the tissue is dissociated by enzymatic digestion. Typically, brain tissue, e.g., cortex, is minced to 1 mm$^3$ size and added to a digestion solution containing a proteolytic enzyme in a calcium and magnesium-free buffered salt solution. Suitable proteolytic enzymes include, e.g., papain and trypsin.

Conditions suitable for dissociating cells and preparing a cell suspension are well known in the art and may be readily practiced by those of skill (see, e.g., Heuttner et al., 1986, *J Neurosci.* 6:3044–60). In an exemplary embodiment described in the remainder of this section, intended to be illustrative and not limiting, the digestion is carried out in 116 mM NaCl, 5.4 mM KCl, 1 mM NaH$_2$PO$_4$, 0.36 glucose, 1 mM EDTA, 0.1% phenol red, 26 mM NaHCO$_3$, 20 U/ml papain, and 0.4 mg/ml L-cysteine. Typically, the enzymatic dissociation is allowed to proceed for about 1 hour (e.g., from about 0.5 h to about 2 h) at 37° C., usually in an atmosphere of 95% oxygen 5% carbon dioxide. It will be appreciated that methods for dissociating tissues to produce dissociated cells may vary, depending, for example, on tissue type and the age of the animals or patients from which tissues are collected. For example, for many adult tissues the digestion solution will contain collagenase (e.g., about 100 to 500 IU/ml).

Following enzymatic digestion, the digestion buffer is replaced by a post-digestion buffer for further processing, removing as much as possible of the papain or other digestion enzyme to maximize the recovery of microglial cells. Typically, the post-digestion buffer includes salts (including magnesium and calcium), a protease inhibitor corresponding to the protease used for enzymatic disaggregation (e.g., 2 mg/ml trypsin inhibitor or fetal calf serum) and protein (e.g., 1 mg/ml BSA). For example, an exemplary post-digestion buffer is Dulbecco's phosphate buffered saline ("DPBS") (Life Technologies) containing 2 mg/ml trypsin inhibitor, 125 units/ml DNase (e.g., Sigma Chemical co., tissue culture grade), and 1 mg/ml BSA. DNase is included to digest genomic DNA released during the enzymatic digestion during disaggregation, which may interfere with subsequent steps and/or affect cell viability.

The tissues are incubated in post-digestion buffer for about 10 minutes at room temperature. The extent of DNA digestion can be easily monitored: When intact genomic DNA is present in the solution, the tissues tend to form clumps, while when genomic DNA is completely digested, the tissue pieces can flow freely in the solution.

The post-digestion buffer is removed, and replaced with fresh buffer (e.g., 1–3 milliliter). The tissues are pipetted through a 1 ml or 10 ml pipet three times (triturated) to dissociate the tissues into cell suspension (with 1 ml pipettes giving a more complete dissociation). The solution is then allowed to sit for 2–5 minutes to allow the undissociated tissue will settle into the bottom, and the dissociated cells are transferred to a new test tube. Additional post-digestion buffer (e.g., 1–3 ml) is added to the tissue, and trituration is repeated, and can be repeated until all the tissues are dissociated into cells suspension. The cell suspension is then passed through the nylon mesh to remove any small pieces of undissociated tissues, and yield a single cell suspension. Other debris and non-cellular material is also removed during this process. The resulting brain cell suspension includes microglial cells, neurons, astrocytes, oligodendrocytes, meningeal cells, and vascular endothelial cells. The dissociation and post-dissociation steps are used to produce a composition containing primarily single cells (i.e., unaggregated cells), e.g., a composition in which at least about 80%, more often at least about 90%, generally at least about 95% single cells), as monitored microscopically.

It will be appreciated that routine steps are taken during cell isolation to maintain the vitality of the microglial cells. For example, in many embodiments, the use of sterile technique is desirable.

As described in detail infra, the resulting cell suspension is contacted with immunoglobulin to which the Fc receptors of the microglial cells bind.

C. Preparation of Immobilized Immunoglobulin i) Source of Immunoglobulin

Microglial cells express an Fc receptor capable of binding IgG (see, e.g., Vedeler et al., 1994, *J Neuroimmunol* 49:19–24). In one embodiment of the invention, the immunoglobulin to which the cell suspension is contacted is IgG, or Fc-containing fragments thereof. In various alternative embodiments, the immunoglobulin comprises IgE, IgM, or IgA, total gamma globulin, or mixtures thereof. IgG and purified Fc fragments may be obtained from numerous sources (e.g., Vector Lab, Burlingame, Calif.; Sigma; Life Technologies, Inc.; Jackson ImmunoResearch Laboratory [cat. nos. 012-000-003 and 012-000-008]) or may be prepared by routine methods (e.g., Harlow & Lane, 1988, *Antibodies A Laboratory Manual*, Cold Spring Harbor Laboratory, New York, and references cited therein). Total gamma globulin is available from Jackson ImmunoResearch Laboratory, West Grove, Pennsylvania (cat.# 012-000-002). Although not critical, the immunoglobulin and microglial cells are generally species matched. For example, when rat microglia are being purified, rat immunoglobulin is used while, if human microglia are being purified, human immunoglobulin is used. However, because of cross reactivity between related species, the match is not critical. For example, mouse IgG may be used to purify rat microglia.

ii) Matrix

The immunoglobulin is immobilized prior to, or subsequent to, being contacted with the microglial cell-containing cell. The matrix to which the immunoglobulin is immobilized is usually plastic (e.g., polystyrene), but may be glass, or other materials. It should be noted that the matrix should not be treated for any enhancement of cell adhesion, because cells can bind nonspecifically on those surfaces. Thus, cell culture or tissue culture dish that have been treated to enhance cell adhesion (e.g., by coating with poly-lysine) are not suitable.

Typically, the matrix is in the form of a plate (e.g., a 60 mm$^2$ or 100 mm$^2$ dish) or bottle, but may be in the form of beads, slides, coverslips, and the like. Suitable plates include bacteriological dishes (e.g., Falcon #1007, Fisher #8757-12), a polystyrene plastic matrix (Applied Scientific #AS-4056), and the like.

iii) Immobilization

IgG is bound to the matrix by adsorption, conjugation, via a specific-binding pair interaction (e.g., biotinylated IgG bound to avidin immobilized on the matrix, or antigen-specific IgG bound to an immobilized antigen), or similar methods.

In one embodiment, the matrix is plastic and the immunoglobulin (e.g., IgG) is immobilized by adsorption. For example, IgG in a buffered solution (e.g., Tris, Hepes, or phosphate buffers, e.g., 50 mM Tris pH 9.5) may be incubated with the matrix for a period of time (e.g., typically overnight at 4° C. or 1.5 h at room temperature). Incubation of IgG in a basic solution (e.g., pH greater than about 9) results in improved binding of IgG to some plastic matrices. Typically the IgG is at a concentration of from about 1 to about 100 pg/ml (usually about 10 pg/ml). When plates are used, about 3 ml antibody solution per 60-mm plate or about 10 ml per 100-mm plate (or the equivalent quantity per surface area for beads or other matrices) may be used. Following adsorption, unbound immunoglobulin is removed (e.g., by washing 3×in 0.15 M NaCl or PBS at room temperature) and the matrix is incubated in washing buffer supplemented with 0.2 mg/ml BSA until use. The coated matrix can be kept for up to 1 week at 4° C. in this solution.

In an alternative embodiments, the immunoglobulin can be immobilized after binding to the target cells. For example, IgG can be combined with the suspension containing microglial cells. The IgG can then be immobilized by incubation with staphylococcal Protein A-coated dishes (resulting in the concurrent immobilization of microglial cells).

D. Adherence of Microglial Cells and Removal of Non-Adherent Cells

The cell suspension is contacted with the immunoglobulin-coated matrix under conditions that result in binding of the microglial cells to the matrix. The cell suspension is typically poured or pipetted onto the matrix (e.g., into a plastic Petri dish) and cells are allowed to settle and adhere for between 30 minutes and 1 hour (typically 45 minutes) at room temperature. Typically, at least $10^7$ cells are added per 100 mm dish (equivalent to 130,000 cells/ $cm^2$). Cell density is important for cell survival in the culture, i.e., survival of purified microglia is higher at higher densities. However, adding more than $10^6$ cells/$cm^2$ will usually decrease the total yield.

Alternatively, the matrix (e.g., immunoglobulin-coated glass or plastic beads) can be immersed into a vessel containing the cell suspension, allowing cells to adhere to the immunoglobulin adherent to the matrix.

The nonadherent cells are removed by washing the matrix (e.g., dishes or beads) with a physiological solution such as DPBS, DMEM, or HBSS. Usually all the nonadherent cells can be removed after 6 to 7 washes. Microscopic observation is usually carried out to make sure that all the nonadherent cells are removed.

The method described here can purify acutely dissociated cortical microglia within hours, and the purity, yield and survival can be monitored throughout the experiment. In one embodiment, cell samples are obtained at various time point in the purification process (including the starting material, e.g., total cortical cells) or post purification culture. Cell numbers (e.g., total cell number) can be determined using any suitable method, e.g., by cell counting with a hemocytometer. Microglial cells may be identified by morphology (see FIG. 1), by their ability to endocytose fluorescently labeled LDL (see FIG. 2; Giulian et al., 1985, *Proc. Natl. Acad. Sci. USA* 82:4287–4290), by immunochemical staining with specific markers such as CD11 (Robinson et al., 1986, *Immunology* 57:239–47), ED1 (Bauer et al., 1994, *J. Neurosci Res* 38:365–75; Milligan et al., 1991, *J Comp Neurol* 314:125–35), or using other assays. Cell viability can be monitored by trypan blue and MTT assays (Mosmann, 1983, *J. Immunol. Meth*. 65:55–63).

E. Purified Population

Using the method of the invention, enriched (i.e., purified) populations of microglial cells are produced. The enriched populations are typically greater than 90% pure, as judged by morphology or function. Usually, populations are at least 95% pure, often at least 98% pure, and frequently at least about 99.5% homogeneous.

Figure 2:
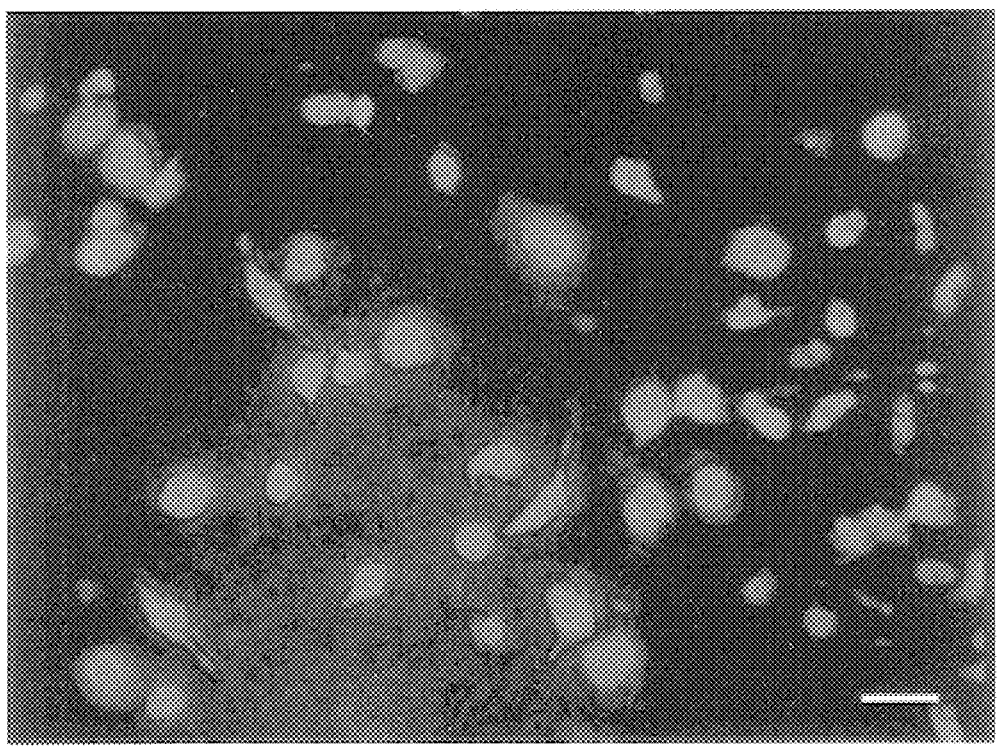
FIG. 2 shows the presence of scavenger receptors in purified rat microglia. Cultured purified microglia were incubated for 4 hours at 37° C. with acetylated low-density lipoprotein, labeled with the fluorescent probe 1,1'-dioctadecyl-3,3,3',3'-tetramethy-liodocarbocyanate (DIL-ac-LDL) (in red). Total cells are visualized by a nuclear dye, DAPI (in blue). Microglia, which possess scavenger receptors on their surface, are able to endocytose the DIL-ac-LDL and become fluorescently labeled. Nearly 100% of the purified cells were labeled by the fluorescent probe, indicating that the culture is a nearly pure population of microglia. Scale bar: 50 μm.

The purified population can be cultured in vitro. In one embodiment, the cells are cultured on the matrix to which the immunoglobulin is immobilized (i.e., without dissociating the cells from the immunoglobulin and transferring them to a cell culture dish). In an alternative embodiment, the cells are dissociated from the immunoglobulin, e.g., by incubating the cells in calcium and magnesium-free DPBS for 5 minutes at 37° C., and then transferred to a cell culture dish or bottle and cultured. Suitable conditions for culture of microglial cells are known in the art and are described in, e.g., Giulian et al., 1985, *Proc. Natl. Acad. Sci. USA* 82:4287–4290, Bottenstein and Sato, 1979, *Proc. Natl. Acad. Sci. USA* 76:514–51. In one embodiment, the microglial cells are cultured in Dulbecco's Modified Eagle Medium ("DMEM") (Life Technologies, Cat.# 11965-092) containing 10% fetal bovine serum, 2 mM, glutamine, 100 units/ml, penicillin, 100 μg/ml streptomycin, and 1 mM sodium pyruvate. FIG. 1 shows cultured purified rat microglia, one week after purification, viewed by phase contrast microscopy. The cells are homogeneous, with typical microglial characteristics of large size and phase dark cell bodies with vacuoles in the cytoplasm.

EXAMPLE 1

Purification of Microglial Cells from Rat Brain

A. Materials and Methods i) Animals

1–2 day old Sprague-Dawley (S/D) rats were used. The rats were ordered from Taconic Farms, Inc. (Germantown, N.Y.). A total of 13 pups were used in this experiment.

ii) Reagents 100 mm Petri dishes were obtained from Applied Scientific, South San Francisco, Calif. (Cat. no. AS-4056). Total rat gamma globulin (Cat.# 012-000-002) and whole rat IgG (Cat.# 012-000-003) are obtained from Jackson ImmunoResearch Laboratory, Inc, West Grove, Pa. Phosphate buffer solution (PBS, Cat.# 20012-027), Dulbecco's PBS (DPBS, Cat.# 14040-117 and 14287-072), Dulbecco's modified eagle medium (DMEM, Cat.# 11965-092), fetal bovine serum (FBS, Cat.# 10082-147), L-glutamine (Cat.# 25030-081), penicillin and streptomycin (Pen-Strep, Cat.# 15140-122), and sodium pyruvate (Cat.# 11360-070) are obtained from Life Technologies, Gaithersburg, Md. Papain (Cat.# 39A2638) is obtained from Worthington, Freehold, N.J. Trypsin inhibitor (Cat.# 109-878) is obtained from Boehringer-Mannheim, Indianapolis, Ind. Bovine serum albumin (BSA, Cat.# A8806), L-cysteine (Cat.# C2529), DNase (Cat.# D-4527), insulin (Cat.# 1-6634) are obtained from Sigma, Saint Louis, Mo.

B. Preparation of IgG-Coated Petri Dishes

Petri dishes were incubated overnight at 4° C. in 12 ml of pH 9.5 Tris (50 mM) containing total rat gamma globulin or whole rat IgG (10 ug/ml). Each Petri dish was washed 3×with PBS. A total of 10 Petri dishes were prepared.

C. Preparation of Total Cortical Cell Suspension

Brain tissue was dissociated by a modification of the procedure of Heuttner et al., 1986, *J Neurosci*. 6:3044–60. 1 to 2 day old S/D rats were decapitated, and the cortexes are dissected in calcium and magnesium-free Dulbecco's PBS (Life Technologies Cat.# 14190-144). The tissues are minced to 1 $mm^3$ size, and enzymatically dissociated for 1 hour at 37° C. with constant blow of 95% oxygen 5% carbon dioxide. The digestion was carried out in 20 ml digestion solution ($Ca^+$, $Mg^+$-free Earle's balanced salt solution; EBSS, 116 mM NaCl, 5.4 mM KCl, 1 mM $NaH_2PO_4$, 0.36 glucose, 1 mM EDTA, 0.1% phenol red and 26 mM NaHCO$_3$) containing papain (20 U/ml) and L-cysteine (0.4 mg/ml). The digested tissues were transferred to a 50 ml test tube.

8 ml of post-digestion buffer ("trituration buffer") was added to the tissue, followed by incubation at room temperature for 5–10 minutes (until all the tissues can float freely in the solution, indicating that the genomic DNA was digested). Trituration buffer is DPBS (Life Technologies cat. no.14287-072) containing trypsin inhibitor (2 mg/ml), DNase (125 units/ml), and BSA (1 mg/ml). The solution was then removed, and the tissues were triturated sequentially in the trituration buffer to yield a suspension of single cells. The cells were recovered by centrifugation at 1000 xg.

D. Purification of Microglial Cells

The total cortical cell suspension were resuspended in 100 ml of DPBS containing 0.04% BSA and 0.5 gg/ml insulin. 10 ml of cell suspension is incubated in each dish coated with total rat IgG for 45 minutes at room temperature, with gentle agitation every 15 minutes. The nonadherent cells are removed by washing the dishes with DPBS (containing calcium and magnesium) seven times.

The dishes were carefully examined under the microscope to ensure that all the nonadherent cells were removed. The cells adhered on the panning dish were microglia as determined based on morphology.

E. Culture of Microglia Cells

The adherent microglia cells prepared supra were cultured on the IgG-coated panning dishes in 10 ml DMEM containing 10% fetal bovine serum, 2 mM glutamine, 100 units/ml penicillin, 100 ug/ml streptomycin, and 1 mM/ml sodium pyruvate. After the panning, the cells were cultured directly on the panning dish in DMEM/10% FCS. The cells were fed twice a week.

EXAMPLE 2

Characteristics of Purified Microglial Cells

We analyzed the microglial cells prepared in Example 1, to confirm they had properties of normal microglial cells. The results indicate that the purified cells are a pure population of microglia with appropriate physiological characteristics and function.

After 1 to 2 weeks of culture, the microglial cells prepared in Example 1 were collected by trypsin treatment. In brief, the medium was removed and the cells were rinsed with 10 ml calcium and magnesium free-PBS. The cells were then incubated in 5 ml trypsin/EDTA solution (Life technologies, Inc.) for 2–5 minutes. The dissociated cells were then collected in a test tube with 5 ml of medium. The cells were spun down at 1000xg for 5 minutes, and were replated in 96 well culture plate at 50,000 cells/well.

A. Scavenger Receptor Function

One of the characteristics of microglia is their ability to clear lipid from the environment by the scavenger receptor on their surface (Brierley and Brown, 1982, *J Comp. Neurola* 211:397–406). We examined this property on our purified microglia using the DIL-ac-LDL uptake assay (Giulian and Baker, 1986, *J Neuroscience* 6:2163–78).

The cultured purified microglia were incubated for 4 hour at 37 C with acetylated low-density lipoprotein, labeled with the fluorescent probe 1,1'-dioctadecyl-3,3,3',3'-tetramethyl-iodocarbocyanate (DIL-ac-LDL). Nearly 100% of the purified cells were labeled by the fluorescent probe (FIG. 2), indicating that the culture was a nearly pure population of microglia.

B. Microglia Activation Assay

Figure 3:
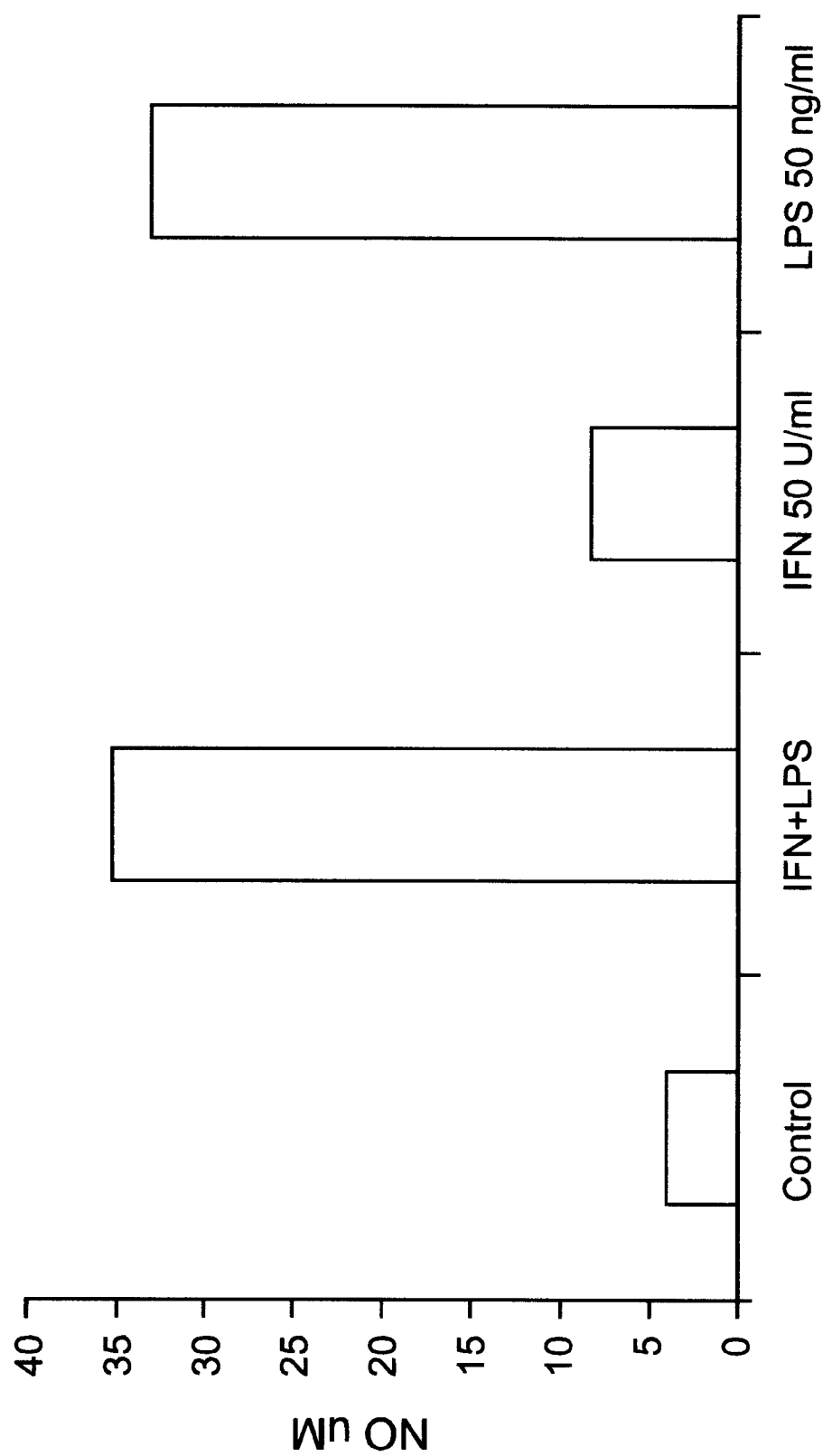
FIG. 3 shows the effect of lipopolysaccharide (LPS) and interferon gamma (IFN) on purified microglia. After 1 to 2 weeks in culture, purified microglia were exposed to 50 U/ml interferon gamma, 50 ng/ml LPS, or both for 48 hours. The media were collected and nitric oxide (NO) concentration was measured. NO concentration increased in cultures with LPS, indicate that the purified microglia responded to LPS and became activated.

To assess the ability of the purified microglial cells to function in an inflammation response, we examined the response of the cultured cells to inflammation stimulants. The cells were stimulated with bacterial lipopolysaccharide (LPS, 50 ng/ml), rat interferon-gamma (IFN-gamma, 50 U/ml), or both. After 48 hours, the media were collected and nitric oxide (NO) concentration was measured using a Nitrate/Nitrite colorimetric assay kit from Cayman Chemical (Ann Arbor MI; Zielasek et al., 1992, *Cell Immunol.* 141:111–20). NO concentration increased in cultures with LPS (FIG. 3), indicating that the purified microglia responded to LPS and became activated (Brierley et al., 1982, *J Comp Neurol.* 211:397–406; Zielasek et al., 1992, *Cell Immunol.* 141:111–20.

All references cited herein are incorporated herein by reference in their entirety and for all purposes to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for obtaining a cell population enriched in microglial cells, said method comprising:
    (a) contacting a composition comprising quiescent microglial cells having $F_c$ receptors from normal animal tissue with immunoglobulin G having an $F_c$ domain wherein the immunoglobulin G is immobilized on a matrix prior to or after said contacting, whereby said $F_c$ receptors on the microglial cells in the composition bind the $F_c$ domain of immunoglobulin G before and after immobilization; and
    (b) removing non-adherent cells, thereby producing cell population enriched in quiescent microglial cells, wherein said cell population enriched in quiescent microglial cells comprises at least 95% microglial cells.

2. The method of claim 1, wherein the immunoglobulin comprises an Fc-containing fragment of immunoglobulin G.

3. The method of claim 1, wherein the immunoglobulin G is immobilized on a matrix prior to said contacting.

4. The method of claim 1, wherein the matrix is a plastic.

5. The method of claim 4, wherein the matrix is polystyrene.

6. The method of claim 5, wherein the matrix is in the form of a dish, coverslip, or bead.

7. The method of claim 1, wherein the microglial cells are from brain.

8. The method of claim 7, wherein the microglial cells are from rat or mouse brain.

9. The method of claim 1, wherein the microglial cells and the immunoglobulin G. are from the same species.

10. The method of claim 7, wherein the microglial cells are human.

11. The method of claim 1, wherein said cell population enriched in microglial cells comprises at least 98% quiescent microglial cells.

12. The method of claim 1, wherein the animal is a human.

13. The method of claim 1, wherein the animal is a non-human primate.

14. The method of claim 1, wherein the animal is a mouse or a rat.

15. The method of claim 1, further comprising culturing microglial cells from the cell population produced in step (b).

16. A method for obtaining a cell population enriched in microglial cells, said method comprising:
contacting a composition comprising microglial cells having $F_c$ receptors with a population of purified Fc fragments from immunoglobulin G, wherein
the purified Fc fragments are immobilized on a matrix prior to or after said contacting,
whereby said Fc receptors on the microglial cells in the composition bind the purified Fc fragments before or after immobilization; and
removing non-adherent cells, thereby producing the cell population enriched in microglial cells, wherein said population enriched in microglial cells comprises at least 95% microglial cells.

17. The method of claim 16, wherein the microglial cells are from brain.

18. The method of claim 16, wherein the microglial cells are human cells.

19. The method of claim 16, wherein the microglial cells are non-human primate cells.

20. The method of claim 19, wherein the microglial cells are rat or mouse cells.

21. The method of claim 16, further comprising culturing microglial cells from the cell population produced in step (b).

22. The method of claim 16, wherein the population of microglial cells are quiescent microglial cells from tissue of a normal animal.

23. The method of claim 16, wherein the population of microglial cells are activated.

24. The method of claim 16, wherein the microglial cells are from rat or a mouse.

25. The method of claim 16, wherein the cells are from an animal with a neurological disease.

26. The method of claim 16, wherein said cell population enriched in microglial cells comprises at least 98% microglial cells.

* * * * *